United States Patent [19]

Nassi et al.

[11] Patent Number: 5,078,148
[45] Date of Patent: Jan. 7, 1992

[54] APPARATUS AND METHOD FOR CONTINUOUSLY MEASURING VOLUMETRIC BLOOD FLOW USING MULTIPLE TRANSDUCERS AND CATHETER FOR USE THEREWITH

[75] Inventors: Menahem Nassi; Paul D. Corl, both of Palo Alto; Ronald G. Williams, Menlo Park; Mark W. Cowan, Fremont; Jerome Segal, Palo Alto, all of Calif.

[73] Assignee: Cardiometrics, Inc., Mountain View, Calif.

[21] Appl. No.: 508,309

[22] Filed: Apr. 12, 1990

Related U.S. Application Data

[62] Division of Ser. No. 254,317, Oct. 5, 1988, Pat. No. 4,947,852.

[51] Int. Cl.⁵ ............................................. A61B 8/12
[52] U.S. Cl. ............................ 128/661.09; 128/661.10; 73/861.25
[58] Field of Search ................... 128/662.06, 661.08, 128/661.09, 661.10; 73/861.25

[56] References Cited

U.S. PATENT DOCUMENTS

| | | | |
|---|---|---|---|
| 3,542,014 | 11/1970 | Peronneau | 128/662.06 |
| 4,237,729 | 12/1980 | McLeod et al. | 128/662.06 |
| 4,259,870 | 4/1981 | McLeod et al. | 128/662.06 |
| 4,637,401 | 1/1987 | Johnston | 128/662.06 |
| 4,671,295 | 6/1987 | Abrams et al. | 128/662.06 |
| 4,733,669 | 3/1988 | Segal | 128/662.06 |

Primary Examiner—Francis Jaworski
Attorney, Agent, or Firm—Flehr, Hohbach, Test, Albritton & Herbert

[57] ABSTRACT

Apparatus for measuring volumetric flow of a liquid in a vessel having a wall and having an axis extending longitudinally of the vessel parallel to the vessel wall. A flexible catheter is adapted to be disposed in the vessel. First and second ultrasonic transducers are carried by the catheter on one side of the catheter and face the wall of the vessel so that the beams from the transducers each cross substantially the longitudinal axis of the vessel. The first transducer beam is inclined at an angle with respect to the longitudinal axis of the vessel. The second transducer beam is inclined in a direction which is generally perpendicular to the longitudinal axis of the vessel.

9 Claims, 6 Drawing Sheets

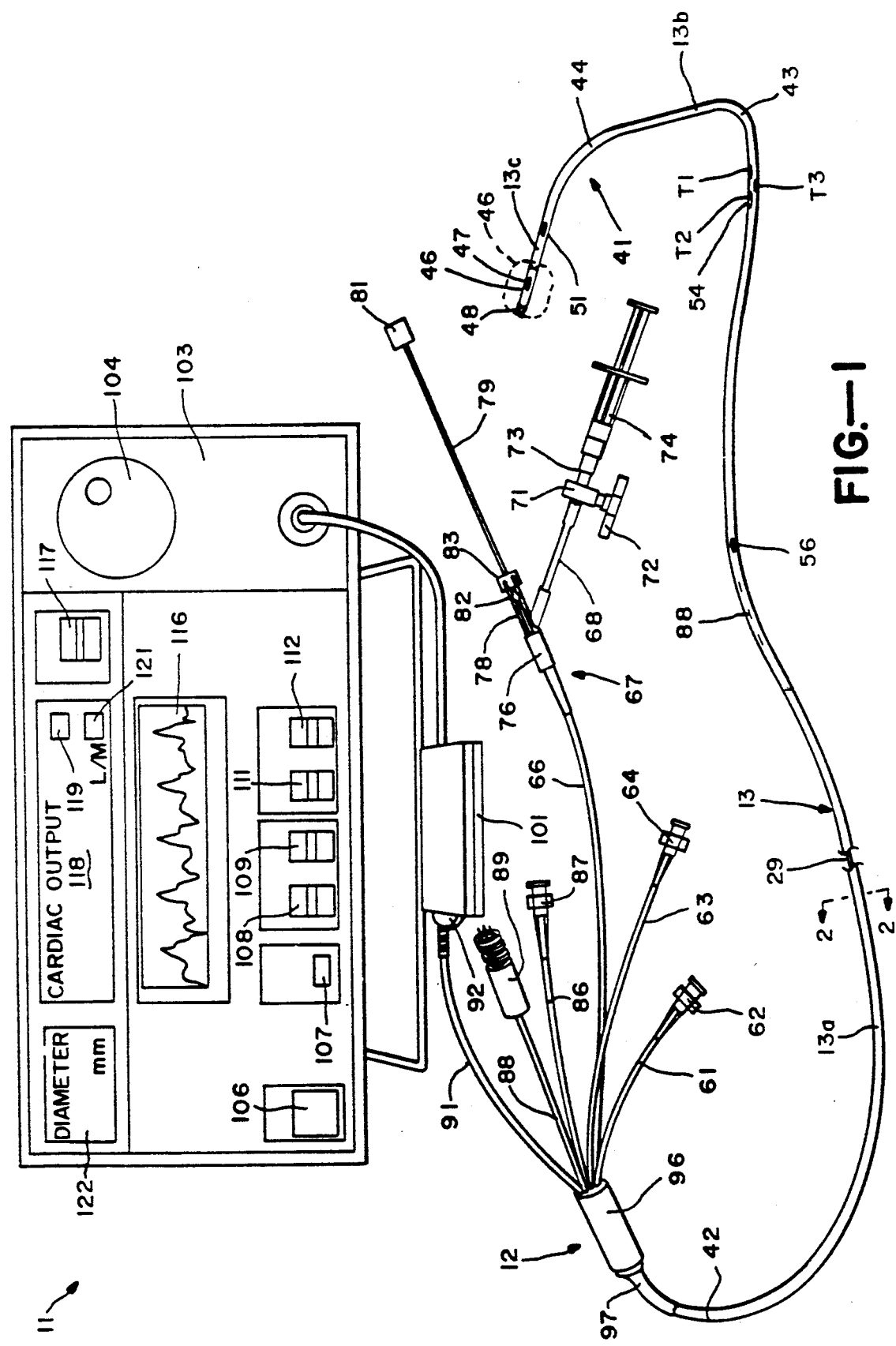
FIG.—1

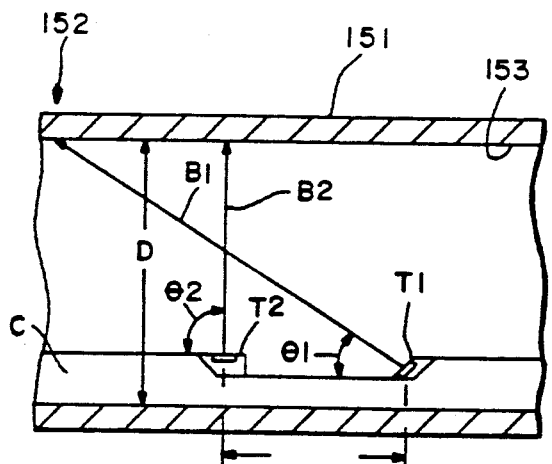
FIG.—3
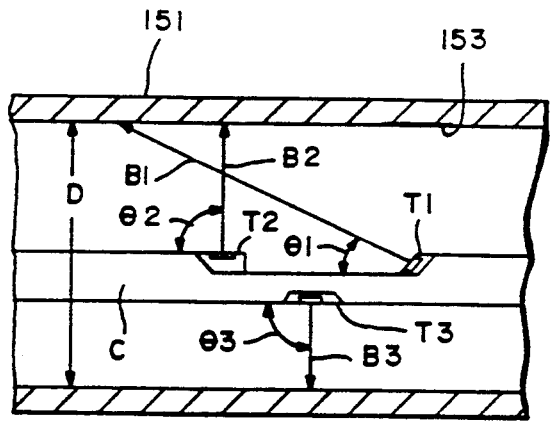
FIG.—4
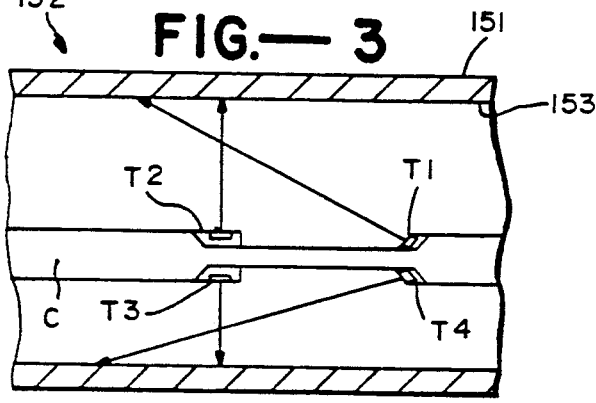
FIG.—5
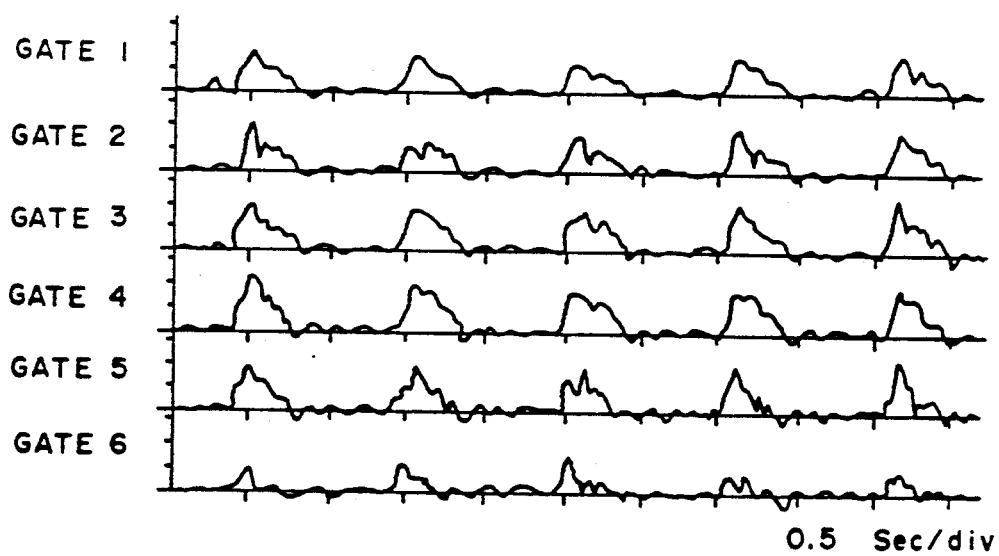
0.5 Sec/div
FIG.—6

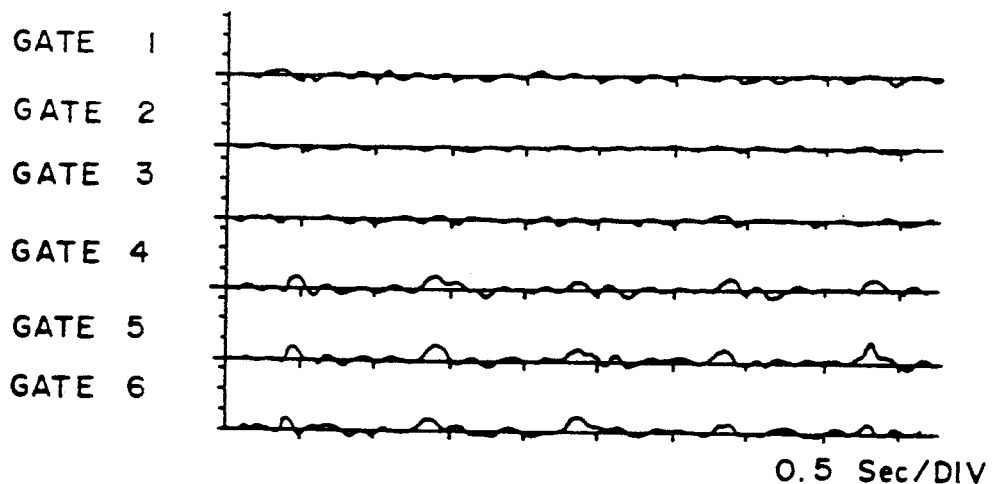
FIG.—7
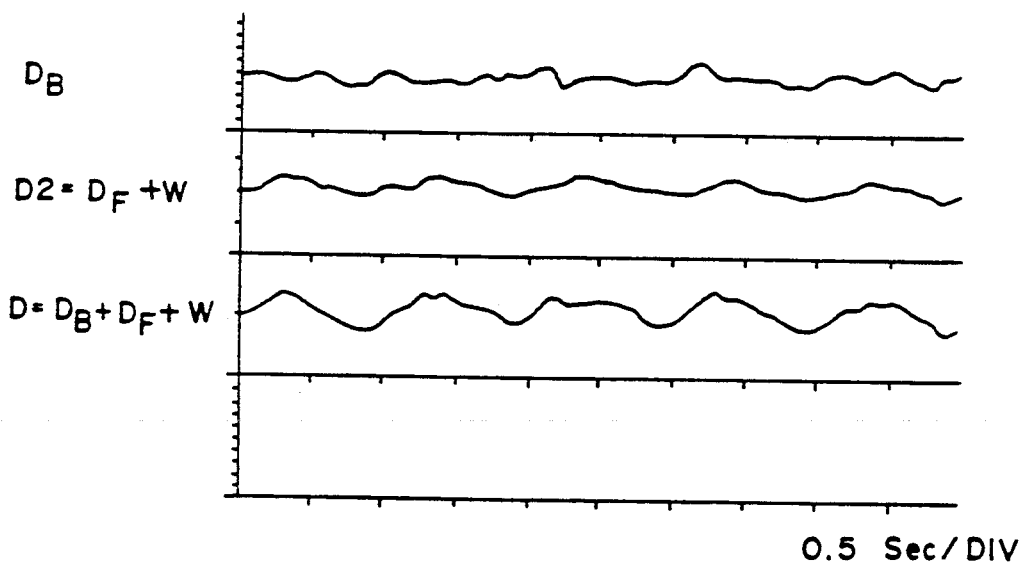
FIG.—8
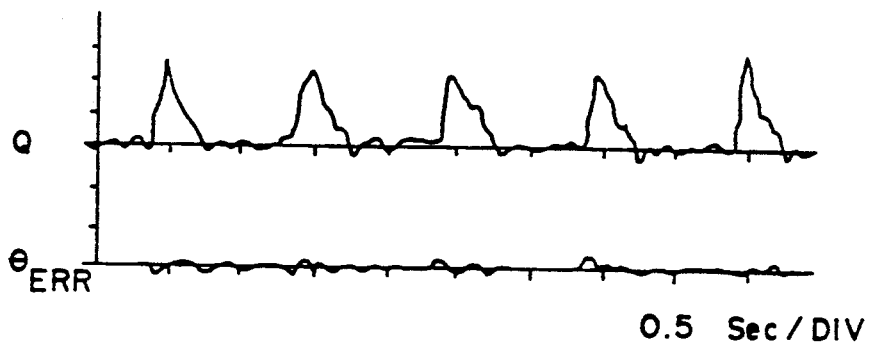
FIG.—9

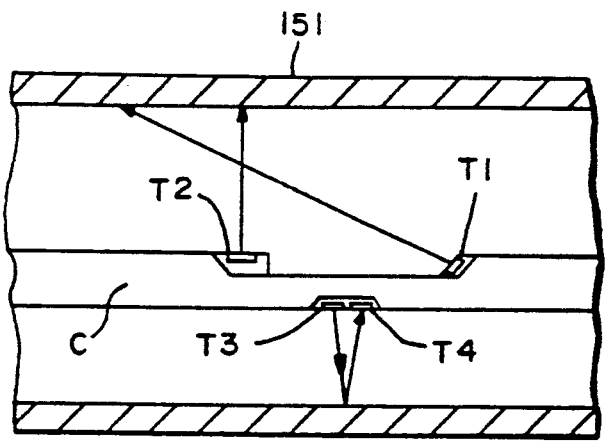
FIG.—10
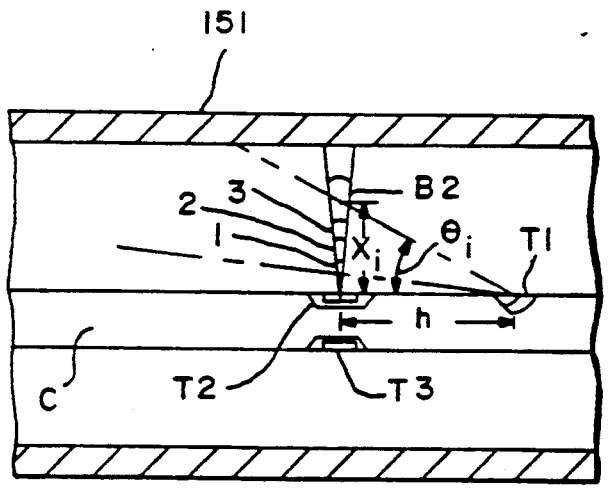
FIG.—11
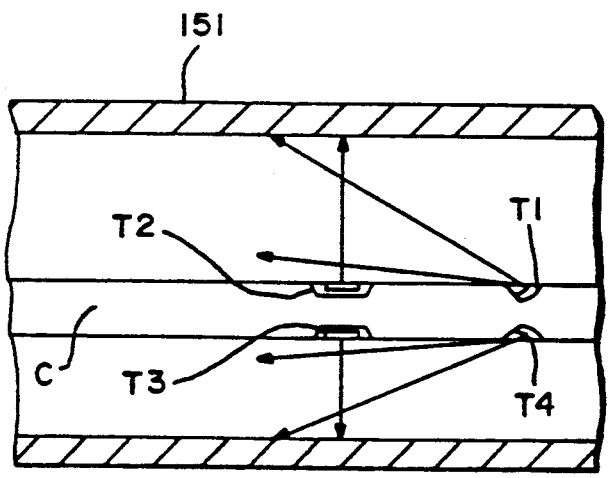
FIG.—12

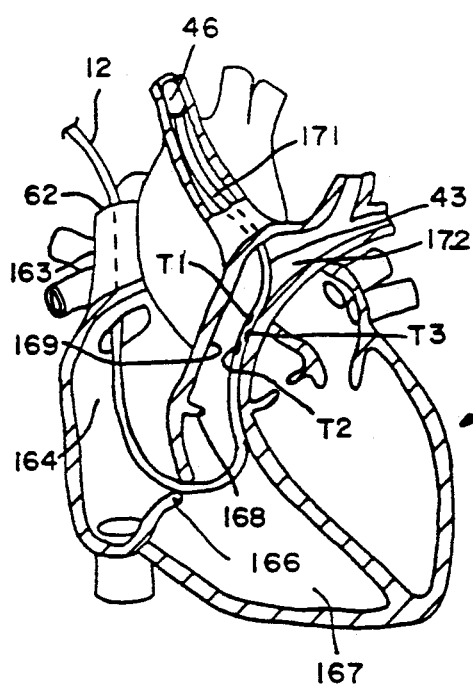
FIG.—13
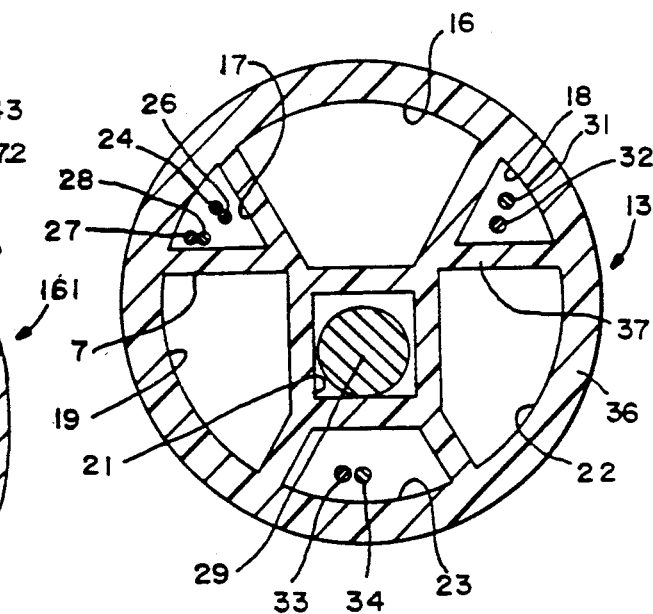
FIG.—2
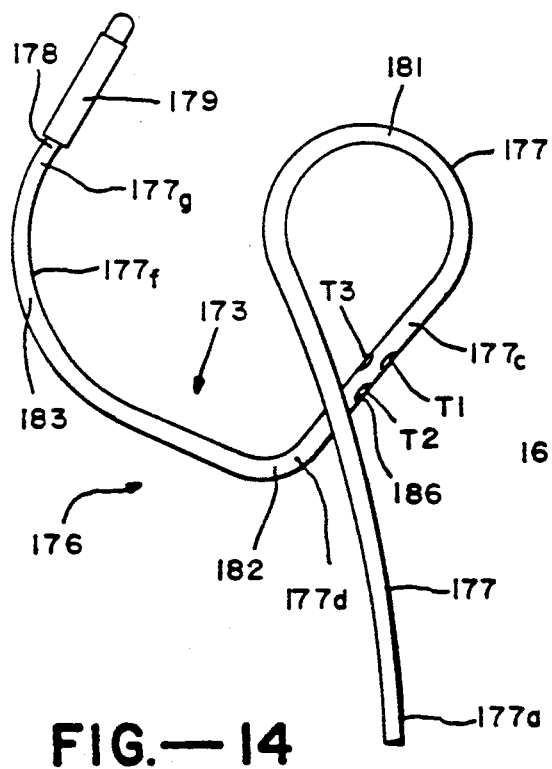
FIG.—14
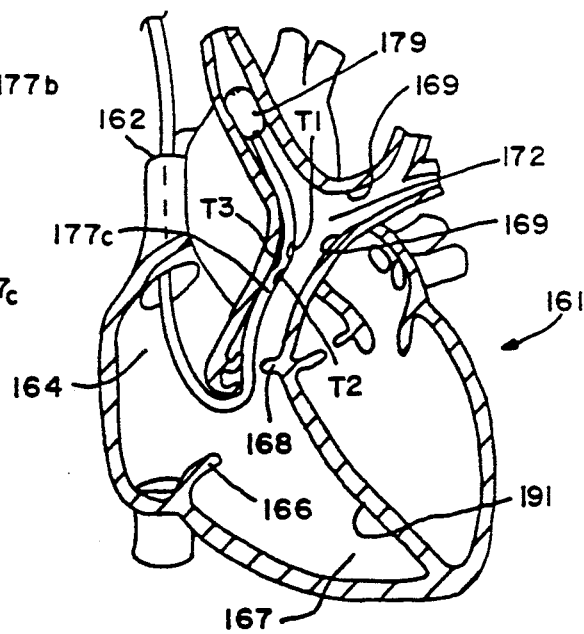
FIG.—15

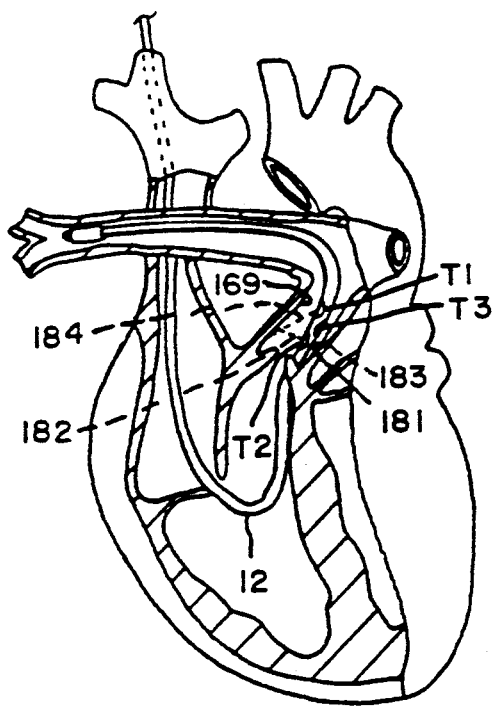
FIG.—16
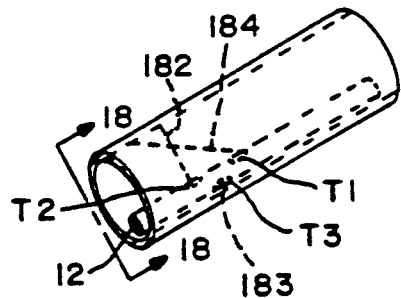
FIG.—17
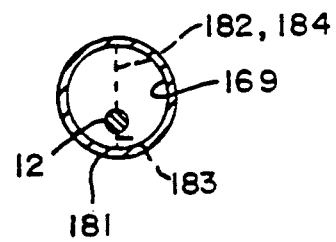
FIG.—18
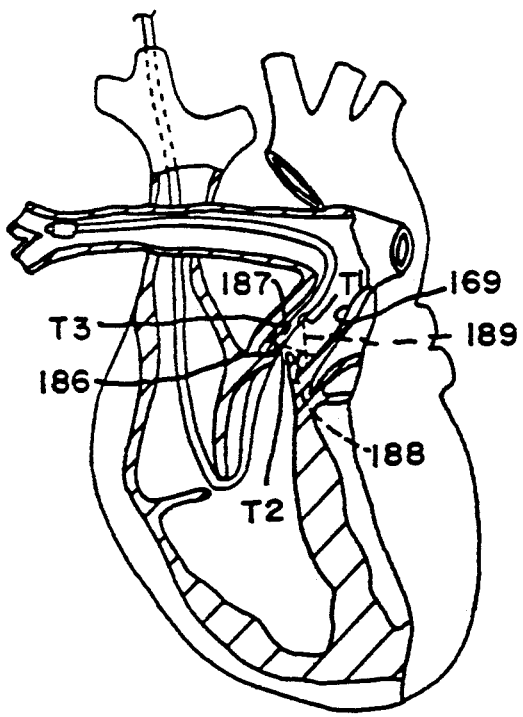
FIG.—19
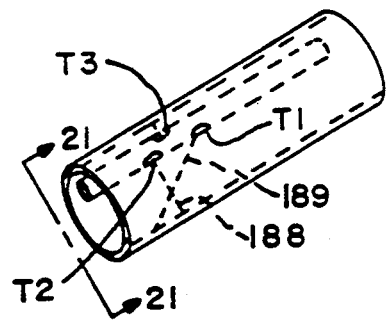
FIG.—20
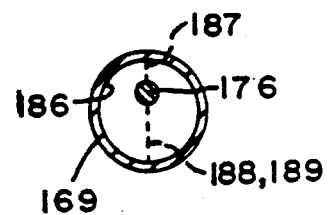
FIG.—21

APPARATUS AND METHOD FOR CONTINUOUSLY MEASURING VOLUMETRIC BLOOD FLOW USING MULTIPLE TRANSDUCERS AND CATHETER FOR USE THEREWITH

This is a division of application Ser. No. 254,317 filed 10-5-88 and now U.S. Pat. No. 4,947,852.

This invention relates to an apparatus and method for measuring blood flow utilizing multiple transducers and more particularly an apparatus and method for continuously measuring volumetric flow using multiple transducers and more particularly, transducers using pulsed Doppler ultrasonics.

In Letters U.S. Pat. No. 4,733,669, there is disclosed a single transducer catheter for measuring blood flow in the pulmonary artery. The measurement technique using such a single transducer makes it necessary to obtain both diameter and velocity measurements with the same transducer beam. As disclosed in the subject patent, it is intended that the transducer be positioned against the wall of the vessel in such a fashion that the beam from the ultrasonic transducer crosses the center of the vessel at an angle such that both vessel diameter and flow velocity can be ascertained. In using such an apparatus and method, a compromise is made in choosing the ultrasonic beam angle to meet the separate requirements of diameter measurement and velocity profile measurement. For optimal diameter detection using a time-of-flight measurement (A-mode), the ideal beam angle is 90° to the axis of the vessel. At this steep angle, the strongest possible vessel wall reflection is obtained, and the measurement is least sensitive to any uncertainty in the beam angle. For optimal velocity measurement, a shallow beam angle (in the range of 30° to 45°) is desirable to minimize the sensitivity of the velocity measurement to uncertainty in the beam angle, while at the same time permitting velocity profile measurement across the entire vessel lumen. Typically, a beam angle in the range of 60° to 70° is chosen for a single transducer catheter, resulting in significant compromises in both the diameter and velocity measurements. Accordingly, there is a need for blood flow measurement apparatus and a method which optimizes the measurement of both diameter and velocity. In addition it has been found that when utilizing a single transducer catheter with the need to position the same against the vessel wall, it is necessary to limit the forces applied by the catheter to the vessel wall to minimize tissue damage in the wall of the vessel. Thus, there is also a need for an apparatus and method which minimizes such potential wall damage.

In general, it is an object of the present invention to provide an apparatus and method for continuously measuring volumetric blood flow which makes use of multiple ultrasonic transducers disposed within a catheter for making time-of-flight (A-mode) diameter measurements and Doppler velocity profile measurements in a vessel. The distal extremity of such a catheter lies in the same plane as the axes of the beams from the transducers, with each beam axis crossing the longitudinal axis of the vessel.

Another object of the invention is to provide an apparatus and method of the above character for continuously measuring volumetric blood flow which makes use of at least two front ultrasonic transducers disposed within a catheter that lies adjacent to a vessel wall for making diameter and velocity measurements.

Another object of the invention is to provide an apparatus and method of the above character in which one or two additional back ultrasonic transducers or at least three ultrasonic transducers have been provided so that accurate diameter measurements can be made even though the catheter does not lie adjacent to a wall of the vessel.

Another object of the invention is to provide an apparatus and method of the above character in which two front and two additional back ultrasonic transducers or at least four ultrasonic transducers have been provided within the vessel for making front and back diameter and velocity profile measurements when the catheter does not lie adjacent to a wall of the vessel.

Another object of the invention is to provide an apparatus and method of the above character in which a ratio of Doppler shift components measured from two or more angles along a given flow streamline using two or more transducers is used to derive an angle error.

Another object of the invention is to provide an apparatus and method of the above character in which angle errors in both the diameter and velocity measurements can be corrected.

Another object of the invention is to provide an apparatus and method of the above character in which the distal extremity of the catheter is formed so as to facilitate the measurement of both diameter and velocity profile within the main pulmonary artery.

Another object of the invention is to provide an apparatus and method of the above character in which the distal extremity of the catheter is formed so that the ultrasonic transducers can be positioned within the main pulmonary artery with their acoustic beams each lying substantially within a single plane which includes the longitudinal axis of the vessel and reflecting off of a segment of the opposite main pulmonary artery wall in a region above the pulmonary valve and below the pulmonary artery bifurcation.

Another object of the invention is to provide an apparatus and method of the above character particularly adapted for short or curved main pulmonary arteries where both diameter and velocity profile measurements are obtained along a beam used for diameter measurement which is substantially perpendicular to and crosses the longitudinal axis of the vessel, thereby minimizing the length of vessel along which the velocity profile is assumed to remain constant.

Another object of the invention is to provide an apparatus and method of the above character in which the diameter and velocity profile measurements are obtained substantially simultaneously.

Another object of the invention is to provide an apparatus and method of the above character in which thermodilution measurements can also be made.

Another object of the invention is to provide an apparatus and method of the above character in which a plurality of pressure measurements, as for example, right atrial, pulmonary artery, and pulmonary capillary wedge pressure measurements can be made in addition to the thermodilution and doppler-based flow measurements hereinbefore described.

Another object of the invention is to provide an apparatus and method of the above character in which the catheter materials are chosen so as to facilitate the pressure, thermodilution, and Doppler-based flow measurements within the pulmonary artery as hereinbefore described.

Another object of the invention is to provide an apparatus and method of the above character in which the catheter material is chosen in combination with its distal extremity geometry to provide stable transducer beam location within a single plane which includes the longitudinal axis of the main pulmonary artery.

Additional objects and features of the invention will appear from the following description in which the preferred embodiments are set forth in detail in conjunction with the accompanying drawings.

FIG. 1 is an isometric view of an apparatus for continuously measuring volumetric blood flow (e.g. cardiac output) using multiple transducers incorporating the present invention.

FIG. 2 is a cross-sectional view taken along the line 2—2 of FIG. 1.

FIG. 3 is a schematic illustration of a catheter of the apparatus of the present invention disposed within a vessel for obtaining a volumetric flow rate using two transducers on the front side of the catheter.

FIG. 4 is a schematic illustration of another catheter incorporating the present invention utilized in a vessel in which three transducers are utilized to obtain a volumetric flow rate by utilizing two front transducers and a back transducer.

FIG. 5 is a schematic illustration of another embodiment of the catheter incorporating the present invention utilized for measuring volumetric flow rate in a vessel by the use of two front transducers and two back transducers.

FIG. 6 is a graph showing flow velocities measured at six different range gates extending across the lumen of the vessel by the use of a first transducer.

FIG. 7 is a chart similar to FIG. 6 showing the flow velocities measured by a second transducer at six different range gates.

FIG. 8 is a graph showing the measurements made for determining the diameter of the lumen of the vessel.

FIG. 9 is a graph showing the volumetric flow rate and the angle error.

FIG. 10 is a schematic illustration of a catheter incorporating the present invention used for measuring volumetric flow rate in a vessel by the use of two front transducers for A-mode front distance and pulsed Doppler velocity profile measurements and two back transducers for use in pitch-catch mode for back distance measurement when the catheter is in close proximity to the back wall, as for example, less than approximately 5 millimeters from the back wall.

FIG. 11 is a schematic illustration of another embodiment of the catheter incorporating the present method using two front transducers for A-mode front distance measurement and pitch-catch mode pulsed-Doppler velocity profile measurement, and a single back transducer for A-mode back distance measurement.

FIG. 12 is a schematic illustration of still another embodiment of a catheter incorporating the present invention utilized to measure volumetric flow rate in a vessel in which the catheter is provided with first and second front transducers and third and fourth back transducers and in which pitch-catch modes are used to measure Doppler velocity profiles on the front and back sides of the catheter and A-modes are used to measure front and back distances to the vessel walls.

FIG. 13 is a cross-sectional view of a human heart showing the manner in which the standard catheter shown in FIG. 1 lies adjacent the wall of the pulmonary artery.

FIG. 14 is a plan view of the distal extremity of another embodiment of a catheter of the present invention which can be utilized for hugging the wall of the pulmonary artery of the heart as shown in FIG. 15 and thus can be called a "huggy-type" catheter.

FIG. 15 is a cross-sectional view of a human heart showing the manner in which the huggy-type catheter shown in FIG. 14 engages the wall of the pulmonary artery.

FIG. 16 is a cross-sectional view of a human heart showing the catheter of FIG. 1 positioned within the pulmonary artery.

FIG. 17 is an enlarged fragmentary isometric view of a portion of the main pulmonary artery with the catheter positioned as in FIG. 16.

FIG. 18 is a cross-sectional view taken along lines 18—18 in FIG. 17.

FIG. 19 is a view similar to FIG. 16 showing the "huggy-type" catheter of FIG. 14 positioned within the pulmonary artery.

FIGS. 20 and 21 are views similar to FIGS. 17 and 18 with the catheter positioned as in FIG. 19.

In general, the apparatus for measuring volumetric flow of a liquid in a vessel having a wall and having an axis extending longitudinally of the vessel and parallel to the vessel wall is comprised of a flexible catheter adapted to be disposed within the vessel. First and second ultrasonic transducers are carried by the catheter on one side of the catheter and face the opposite wall of the vessel to provide diameter and velocity measurements. The first transducer beam is inclined at an angle with respect to the longitudinal axis of the vessel. The second transducer beam is oriented in a direction which is generally perpendicular to the longitudinal axis of the vessel. In order to permit the catheter to move off of the wall of the vessel and still make accurate diameter and velocity measurements, an additional transducer is provided on the back side of the catheter opposite the second transducer, facing in a direction generally opposite that of the second transducer so that a relatively accurate vessel diameter measurement can be made regardless of the spacing of the catheter from the vessel wall.

In the method for measuring volumetric flow of liquid in a vessel having a wall and having an axis extending longitudinally of the vessel and parallel to the vessel wall, a flexible catheter is provided which is adapted to be disposed within the vessel. The catheter carries at least two ultrasonic transducers on one side of the catheter. One of the transducers is positioned such that its beam is oriented at a substantial angle with respect to the longitudinal axis of the vessel to provide a Doppler shift velocity profile measurement. The second transducer is positioned so that its beam is substantially perpendicular to the longitudinal axis of the vessel to provide an ultrasonic A-mode time-of-flight diameter measurement. When the catheter is not positioned against the wall of the vessel, an additional transducer is provided which is carried by the catheter and faces in a direction opposite the second transducer so as to make possible accurate vessel diameter measurements.

More specifically, the apparatus and method for continuously measuring volumetric blood flow using multiple transducers is shown in FIG. 1. As shown therein the apparatus consists of a control console 11 and a catheter 12 which is connected to the control console 11. The catheter 12 consists of a flexible elongate member 13 formed of suitable material such as plastic. A cross-sectional view of the elongate member 13 is shown in FIG. 2 and as shown therein, the flexible elongate member 13 is provided with a plurality of lumens 16, 17, 18, 19, 21, 22 and 23 for a total of 7 lumens. As shown, the lumens are of various sizes and perform different functions. For example, lumen 16 is utilized for providing proximal or main pulmonary artery pressure and it accommodates the front distal and proximal transducers. Lumen 17 is provided for the front proximal and distal transducer wires 24, 26, 27 and 28. Lumen 18 is provided for the thermistor and the thermistor wires 31 and 32. Lumen 19 is utilized for providing distal or pulmonary wedge pressure. Lumen 21 is provided for a guide wire 29 and also serves as a balloon inflation and deflation lumen. Lumen 22 is used to provide the right atrial pressure and also serves as an injectate lumen. Lumen 23 accommodates the back transducer(s) and wires 33 and 34 for one or two back transducers when they are provided.

It has been found that these seven lumens can be provided in flexible plastic tubing 13 having an outside diameter of 0.98 inches plus or minus 0.003 inches. The outside circular wall 36 has a minimum thickness of approximately 0.007 inches. The septa 37 dividing the lumens should have minimum thicknesses of approximately 0.004 inches.

As can be seen from FIG. 1, the distal extremity or tip 41 of the elongate member 13 is generally U-shaped. The flexible elongate member 13 is provided with a substantially straight flexible portion 13a having a length of approximately 110 centimeters. The U-shaped tip 41 configuration has a length of approximately 15 centimeters. The flexible elongate member 13 is provided with another relatively straight portion 13b extending beyond an approximately 90° bend 43. It also is provided with another generally straight portion 13c extending beyond a more gently curved approximately 60° bend 44.

An inflatable balloon 46 is mounted on the distal extremity of the portion 13c by suitable means such as an adhesive. The balloon is formed of a suitable material such as latex and can be inflated and deflated by a fluid passing through an inflation and deflation port 47 which is in communication with the balloon inflation lumen 21. The balloon 46 will take a generally spherical configuration as shown in dotted lines when inflated and can be inflated to a suitable diameter as, for example, 10 to 14 millimeters. As can be seen the portion 13c extends through the balloon and is provided with a distal pressure port 48 which is in communication with the lumen 19.

A thermistor 51 of a conventional construction is mounted in the portion 13c proximal of the balloon 46 intermediate of the bend 44 and the balloon 46. It is mounted in the space occupied by the lumen 18. The thermistor 51 is connected to conductors 31 and 32 which extend through the lumen 18.

Additional ports are provided in the catheter 12 and include a main pulmonary artery port 54 which is in communication with the lumen 16 and a right atrial pressure port and injectate port 56 which is in communication with the lumen 22. Both of the ports 54 and 56 are located near the distal extremity of the flexible elongate member 13 with the port 54 being located from 1.3 to 2.5 centimeters from the proximal end of the bend 43 and the port 56 being located approximately 18 centimeters from the port 54.

The proximal extremity of the elongate member 13 is connected to a plurality of fittings through a manifold moulding 96 as shown in FIG. 1. Thus there is provided an elongate flexible member 61 which is provided with a Luer-type fitting 62. The flexible elongate tubular member 61 is connected to the right atrial pressure lumen 22. Another elongate flexible tubular member 63 is provided with a Luer-type fitting 64 and is connected to the distal pressure lumen 19. Another flexible elongate member 66 is connected to the balloon inflation lumen 21. A two arm adapter 67 is mounted on the tubular member 66 that is connected by a flexible tubular member 68 to a stop cock 71 which is provided with a handle 72 and a Luer-type fitting 73. A syringe 74 of a conventional type is provided which carries a fluid of a suitable type such as carbon dioxide which can be used for inflating and deflating the balloon 46. The adapter 67 is also provided with a central arm 76.

The guide wire 29 serves as a positioning and straightening device and extends through the lumen 21 and has a suitable diameter such as 0.012 inches. The guide wire 29 is formed of a suitable material such as stainless steel and is attached to a relatively straight piece of hypodermic tube 79 having a suitable diameter such as 0.042 inches and is also formed of a suitable material such as stainless steel. The tube 79 has a length such that it extends approximately the entire length of the flexible elongate member 66. A knob 81 is secured to the proximal extremity of the tube 79 and is used for advancing and retracting the guide wire 29. The guide wire 29 has a length so that when the knob is pushed forward into the central arm 76, the guide wire 29 extends through to the distal extremity or tip 41 of the catheter 12 to substantially straighten the same to facilitate insertion of the catheter 12 into the vessel of the human body and also to facilitate advancement of the same as the inflated balloon 46 is utilized to advance the catheter as hereinafter described. A solder joint 82 is used for securing the guide wire 29 to the tube 79 and also serves as a stop to prevent retraction of the tube 79 through a removable cap 83 carried by the central arm 76. The solder joint 82 holds the proximal extremity of the wire 29 to the tube 79.

Another flexible elongate element 86 with a Luer-type fitting 87 is provided which is in communication with the main pulmonary artery pressure lumen 16. Another flexible elongate tubular member 88 is in communication with the lumen 18. It is provided with a thermodilution connector 89 of a conventional type. Another flexible elongate member 91 is provided which has wires extending therethrough which are connected to the back transducer provided in the lumen 23 and the front transducer wires provided in lumen 17. The elongate member 91 is connected to a connector 92 which is connected to all of the wires extending through the elongate member 91. A manifold moulding 96 is provided around the proximal extremity of the flexible elongate member 13 and the distal extremities of the flexible elongate members 61, 63, 66, 86, 88 and 91. A strain relief and reinforcing member 97 formed of a suitable material such as rubber extends out of the moulding 96 and covers the proximal extremity 42 of the flexible elongate element 13.

The connector 92 plugs into its corresponding connector 101 which is at the end of cable 102 that extends into the front panel 103 of the control console 11. As shown in FIG. 1, the control console includes a knob 104 provided on the front panel 103 which can be utilized for setting the alarm settings of the cardiac output limits and the diameter limits of the apparatus. A "power on" push button 106 is provided as well as an alarm muting push button 107. In addition, push buttons 108 and 109 can be provided for setting "alarm on", and "high" and "low" alarm limits for the cardiac output.

Similarly, push buttons 111 and 112 can be provided for setting "alarm on", and "low" and "high" alarm limits for the diameter measurement. A graphic screen 116 is provided for displaying instantaneous flow waveforms, flow trends or velocity profiles. Mode push buttons 117 are provided for selecting either a "monitor" or "insert" mode. A digital readout 118 is provided for displaying the cardiac output in liters per minute with push buttons 119 and 121 giving the capabilities to provide the mean cardiac and the peak cardiac outputs. In addition, a digital display 122 is provided for giving a readout of the measured diameter in millimeters.

In accordance with the present invention, to obtain the type of information which is provided by the console 11, at least two ultrasonic transducers are carried by the catheter 12. Front and back transducers are provided as hereinafter described. The front transducers typically are mounted within the recess provided by the lumen 16 whereas the back transducers are provided in the lumen 23 which is diametrically opposite the lumen 16. Various arrangements of the transducers are possible and are described hereinafter in conjunction with FIGS. 3 through 5. In all these arrangements, the distal extremity bends 43 and 44 are formed within the plane which includes the longitudinal axis of the catheter and a line passing diametrically through the catheter and through the middle of the front and back transducer lumens 16 and 23 respectively. This is necessary to orient the transducer beams such that each lies substantially within a single plane which includes the longitudinal axis of the main pulmonary artery when the catheter's distal extremity 13c is positioned downstream in one of the smaller branches of the right pulmonary artery as shown in FIGS. 16 through 21. This beam positioning is essential to obtain accurate diameter and velocity profile measurements for calculating volumetric blood flow or cardiac output.

In FIG. 13, the catheter 12 is shown positioned within a human heart. The introduction of the catheter 12 through the jugular vein of the patient is a technique which is generally well known to those skilled in the art. In order to facilitate introduction, the guide wire 29 is advanced to its extreme distal position by operation of the knob 81 to straighten the distal extremity or tip 41 of the catheter 12 to facilitate introduction of the catheter into the jugular vein of the patient. The catheter 12 as shown in FIG. 13 passes into the heart 161 through the venous port 162 of the superior vena cavae 163, through the right atrium 164, and then through the tricuspid valve 166, the right ventricle 167, through the pulmonary valve 168, through the main pulmonary artery 169 and into the right pulmonary artery branch 171 and then wedging downstream in one of the secondary branches leading from the right pulmonary artery branch with the tip of the catheter having the balloon thereon being disposed in that branch. In the course of inserting the catheter, its location can be monitored by observing the pressure waveforms which are quite distinct from one another in the different parts of the circulatory system.

It can be seen from FIGS. 3 and 13 that the catheter is positioned in such a manner that the front and back transducers carried by the same are positioned within the pulmonary trunk or the main pulmonary artery 169 so that their respective beams lie within a plane which includes the longitudinal axis of the vessel, thereby facilitating accurate diameter and velocity profile measurements. This positioning of the transducers is facilitated by the U-shaped tip 41 of the distal extremity of said catheter, such U-shaped bend acting to center the distal extremity of the catheter within the distal portion of a curved vessel, such as the pulmonary artery. Said catheter is constructed of flexible material which is resilient and resistant to creep and to tensile or torsional strain, with a Shore hardness of 40D-55D. This combination of material properties prevents torsion of the distal extremity of the catheter out of the central plane which includes the longitudinal axis of the vessel and thereby facilitates the proper orientation of the transducer beams within the plane which includes the distal extremity 13c of the catheter and the longitudinal axis of the vessel.

FIGS. 16 through 21 show the distal extremity geometry which in combination with the catheter material, provides the required stable transducer beam directions with each of the beams lying substantially within a single plane which includes the longitudinal axis of the main pulmonary artery.

In FIG. 3, there is shown a schematic illustration of the simplest embodiment of the present invention in which two transducers are utilized to obtain accurate diameter and velocity measurements by assuming that the catheter 12 can be positioned adjacent the wall 151 of a vessel such as the main pulmonary artery. The catheter C is disposed in the vessel lumen 153 and has proximal and distal front ultrasonic transducers T2 and T1 of a suitable frequency and size, as for example, ranging from 6 MHz to 15 MHz in frequency and ranging from 0.5 mm to 1.5 mm in size. These transducers provide ultrasonic beams B2 and B1 respectively. The transducers T2 and T1 are separated by a suitable distance, as for example, ranging from 5 to 15 millimeters. It is assumed that the transducers T2 and T1 are adjacent or against the wall except for the thickness of the catheter C which typically can have a thickness of 2.5 millimeters. Also in FIG. 3, the angle $\theta_1$ is the angle of the beam B1 from the transducer T1 with respect to the vessel wall and $\theta_2$ is the angle of the beam B2 from the transducer T2 with respect to the vessel wall.

Pulsed Doppler techniques have been utilized for measuring flow velocity at any position across a vessel within a small sample volume. By providing a plurality of such sample volumes through "range gating", a technique well known to those skilled in the art, a map of the velocity profile within the vessel lumen may be obtained. Typically, a transducer T1 or T2 is excited with short bursts of ultrasound followed by the detection of Doppler shifted energy scattered from the particles in the moving liquid stream, as for example, moving erythrocytes in human blood. This Doppler shift is then used to calculate the velocity of blood flow within a sample volume or volumes within the vessel. The diameter of the vessel may be determined by measuring the time-of-flight for an ultrasonic pulse transmitted from transducer T2 to propagate across the vessel, be reflected by the far wall and return to the same transducer. The timing of the wall echo can be determined by finding a large amplitude signal in the A-mode scan (amplitude scan) waveform since the echoes from the blood cells are so much weaker than the wall echo.

Flow rate may be calculated if the space average velocity and cross-sectional area of the vessel are known. The space average velocity may be estimated if the velocity is known, simultaneously, at a number of different locations (sample volumes) within the vessel. Cross-sectional area may be calculated from the vessel diameter, which may in turn be determined from knowledge of the speed of ultrasound in blood and the measurement of the propagation time of an ultrasonic pulse across the diameter of the vessel. Vessel diameter and average velocity measurements necessitate that the axis of ultrasound transmission lies substantially witin a single plane which includes the longitudinal axis of the vessel lumen.

In the diagram shown in FIG. 3, the front proximal transducer T2 transmits an ultrasound beam B2 approximately perpendicular to the vessel wall at an angle $\theta_2$ to provide a distance measurement which when added to the thickness of the catheter C provides the diameter D of the flow passage or lumen 153 of the vessel. The front distal transducer T1 transmits an ultrasound beam at angle $\theta_1$ (e.g. 60°) with respect to the vessel wall 151 to provide Doppler shift velocity measurements at 1 to 8 range gate locations or sample volumes along the ultrasonic beam B1. With this diameter and velocity profile information supplied to the console 11, the volumetric flow rate, as for example, the cardiac output can be ascertained as hereinafter described.

The volumetric flow rate Q in a vessel (e.g. cardiac output) is calculated from the diameter and velocity measurements according to the equation:

$$Q = \left(\frac{\pi D^2}{4}\right) v \qquad \text{Equation 1}$$

where D is the inner diameter of the vessel and v is the spatial average flow velocity parallel to the longitudinal axis of the vessel. The vessel diameter D is determined from a time-of-flight distance measurement according to the equation:

$$D = d \cdot \sin \theta_D \qquad \text{Equation 2}$$

where d is the distance measured across the vessel at ultrasonic beam angle $\theta_D$, the angle of the diameter measuring transducer. The spatial average flow velocity $\bar{v}$ is determined from the Doppler frequency shift measurements according to the equation:

$$v = \frac{c\bar{f}}{2f_o \cos\theta_v} \qquad \text{Equation 3}$$

where c the speed of sound propagation in the fluid (e.g. blood), $f_o$ is the ultrasound transmit frequency (e.g. 10 MHz), $\bar{f}$ is the area weighted average of the mean frequency measurements from each of the individual range gates, and $\theta_v$ is the ultrasonic beam angle of the velocity measuring transducer. Combining equations 1, 2 and 3, the volumetric flow Q can be expressed as:

$$Q = \frac{\pi (d \sin \theta_D)^2}{4} \left[ \frac{c\bar{f}}{2f_o \cos\theta_v} \right] \qquad \text{Equation 4}$$

The advantages of utilizing two transducers in accordance with the present invention, rather than using a single transducer catheter will be considered, particularly in light of the flow measurement errors introduced by angular position uncertainty.

The effect of angle uncertainty upon the volumetric flow rate as measured by a single transducer catheter will be considered first. Let it be assumed that a single transducer T1 is disposed on a catheter so that the beam B1 extending therefrom has a nominal angle $\theta_{1NOM}=60°$. Let it be further assumed that due to positioning inaccuracies, the beam B1 assumes a true angle within the vessel $\theta_{1TRUE}=65°$. In the case of a single transducer catheter, the same beam at angle $\theta_1$ is used for both diameter and velocity measurement. Substituting the nominal and true angles into equation 4 it can be seen that the ratio of the true flow $Q_{TRUE}$ to the nominal flow $Q_{NOM}$ is given by:

$$\frac{Q_{TRUE}}{Q_{NOM}} = \left(\frac{\sin\theta_{1TRUE}}{\sin\theta_{1NOM}}\right)^2 \cdot \left(\frac{\cos\theta_{1NOM}}{\cos\theta_{1TRUE}}\right) \qquad \text{Equation 5}$$

In the specific case of $\theta_{1NOM}=60°$ and $\theta_{1TRUE}=65°$, the ratio of true flow $Q_{TRUE}$ to the nominal flow $Q_{NOM}$ is given by:

$$\frac{Q_{TRUE}}{Q_{NOM}} = \left(\frac{\sin 65°}{\sin 60°}\right)^2 \cdot \left(\frac{\cos 60°}{\cos 65°}\right) = 1.30 \qquad \text{Equation 6}$$

The above calculation shows that for an angle error of 5° there would be approximately a 30% error in the volumetric flow rate as measured with a single transducer catheter.

The effect of angle uncertainty upon the volumetric flow rate as measured by a two transducer catheter will now be considered. As illustrated in FIG. 3, let it be assumed that a first transducer T1 is disposed on a catheter so that the beam B1 extending therefrom has a nominal angle $\theta_{1NOM}=60°$ and a second transducer T2 is disposed on the catheter so that the beam B2 extending therefrom is at angle $\theta_{2NOM}=90°$. Suppose further that due to positioning inaccuracies, the catheter is tilted at a 5° angle so that the true angles of the beams B1 and B2 with respect to the axis of the vessel are $\theta_{1TRUE}=65°$ and $\theta_{2TRUE}=95°$. In this two transducer catheter, the transducer T1 would be used for velocity profile measurement while transducer T2 would be used for diameter measurement. Accordingly, the ratio of the true flow $Q_{TRUE}$ to the nominal flow $Q_{NOM}$ as measured by the two transducer catheter is given by:

$$\frac{Q_{TRUE}}{Q_{NOM}} = \left(\frac{\sin\theta_{2TRUE}}{\sin\theta_{2NOM}}\right)^2 \cdot \left(\frac{\cos\theta_{1NOM}}{\cos\theta_{1TRUE}}\right) \qquad \text{Equation 7}$$

In the specific case of $\theta_{1NOM}=60°$, $\theta_{1TRUE}=65°$, $\theta_{2NOM}=90°$ and $\theta_{2TRUE}=95°$, the ratio of true flow $Q_{TRUE}$ to nominal flow $Q_{NOM}$ is given by:

$$\frac{Q_{TRUE}}{Q_{NOM}} = \left(\frac{\sin 95°}{\sin 90°}\right)^2 \cdot \left(\frac{\cos 60°}{\cos 65°}\right) = 1.17 \qquad \text{Equation 8}$$

From this result, it can be seen that by utilizing two transducers, the error in the volumetric flow rate for a 5° angle error is reduced from 30% for a single transducer catheter to 17% for two transducers. This reduction was achieved by uncoupling the diameter measurement angle $\theta_D$ from the velocity measurement angle $\theta_V$. In this case the diameter measurement angle can be optimized for minimum angle sensitivity by making $\theta_{2NOM} = 90°$, so that nearly all of the flow measurement error can be attributed to velocity measurement error.

It has been found in certain applications of the present invention that it cannot always be assured that the catheter C will lie adjacent to the wall 151 of the vessel 152. However, when the catheter C is positioned away from the wall of the vessel, it generally extends in a direction which is parallel to the longitudinal axis of the vessel. When such is the case, an additional transducer is needed to make the distance measurements required for volumetric flow. In FIG. 4, the catheter C is shown spaced from the wall of the vessel and is near the central longitudinal axis of the vessel. The third transducer T3 is provided on the back side of the catheter C generally opposite the transducer T2 on the front side of the catheter C. In this embodiment the transducer T2 is provided for measuring the distance $D_F$ from the front of the catheter to the vessel wall and the additional transducer T3 is utilized for measuring the distance $D_B$ from the back side of the catheter to the wall of the vessel. The vessel lumen D is obtained as set forth in the equation below:

$$D = D_F + D_B + W \qquad \text{Equation 9}$$

where $D_F$ is the distance from the front transducer T2 to the front vessel wall, $D_B$ is the distance from the rear transducer T3 to the back vessel wall and W is the thickness of the catheter or the distance between the two transducers T2 and T3.

In using this three transducer arrangement, it is assumed that even though the catheter C moves away from the wall of the vessel it remains substantially parallel to the longitudinal axis of the vessel or, in other words, there is no angulation with respect to the vessel wall which could cause errors in the diameter or velocity measurements. Also with such a three transducer arrangement it is assumed that the velocity profile across the vessel 151 is substantially symmetrical, that is, the velocity profile measured by the transducer T1 is assumed to give an accurate estimate of the profile velocity on the back side of the catheter C.

A major source of error in cardiac output measurement using Doppler ultrasound can be attributed to angular uncertainty due to the variability of the human anatomy. It has been shown that with the use of two transducers, one for diameter measurement and one for velocity measurement, the flow measurement error due to angle error is significantly reduced. Furthermore, with the use of two transducers, the angular positioning error can actually be measured and used to correct the volumetric flow computation. In order to measure the angle error, Doppler frequency shift measurements are made by transducers T1 and T2 at the various range gates. Using a single range gate where the beams B1 and B2 intersect assures that both beams measure the same blood velocity vector, however, all of the range gate velocity measurements can be separately corrected for angle error using the geometric relationship given below. The streamline velocity vectors can be decomposed into components along the directions of beams B1 and B2 and a catheter angle error with respect to the axis of the vessel can be estimated. The angle error $\theta_{ERR}$ is given by the equation:

$$\theta_{ERR} = \arctan\left(\frac{\sin\Delta\theta}{\frac{f_{B1}}{f_{B2}} - \cos\Delta\theta}\right) \qquad \text{Equation 10}$$

where $\Delta\theta$ is the angle between the two beams B1 and B2, and $f_{B1}$ and $f_{B2}$ are the Doppler frequency shifts measured along beams B1 and B2 at the same flow streamline.

The $\Delta\theta$ angle can be readily determined since it is the angle between the two transducers T1 and T2 which is fixed and can be measured a priori. This angle does not change because of the relative stiffness of the catheter between the two transducers T1 and T2.

Once the angle error $\theta_{ERR}$ has been measured, the true beam angles can be calculated by adding the angle error $\theta_{ERR}$ to the nominal beam angles according to the equations:

$$\theta_{1TRUE} = \theta_{1NOM} + \theta_{ERR} \qquad \text{Equation 11}$$

and:

$$\theta_{2TRUE} = \theta_{2NOM} + \theta_{ERR} \qquad \text{Equation 12}$$

The true volumetric flow $Q_{TRUE}$ can then be computed from equation 4 by substituting $\theta_{1TRUE}$ for $\theta_V$ and $\theta_{2TRUE}$ for $\theta_D$, that is:

$$Q_{TRUE} = \left(\frac{\pi[d\sin(\theta_{2TRUE})]^2}{4}\right)\left(\frac{cf}{2f_o\cos(\theta_{1TRUE})}\right) \qquad \text{Equation 13}$$

Thus, it can be seen that by using a two transducer catheter, the volumetric flow calculation can be compensated for angle error so that it provides an accurate cardiac output measurement even considering the wide variation of human anatomy. The angle error measurement and compensation takes place on an instantaneous basis making it possible to monitor the volumetric flow at a high sampling rate as compared to a heart cycle as, for example, every 20 milliseconds to provide approximately 50 samples between each heart beat.

It should be appreciated that if desired an additional transducer T4 can be added to the back side of the catheter as shown in FIG. 5 so that distance and velocity measurements can be made on both the front and back sides of the catheter C. The additional velocity information from the back side of the catheter can be utilized to provide an accurate volumetric flow rate in the event that there is asymmetry in the velocity profile across the lumen 153 of the vessel 152 and the catheter C is positioned away from the back wall and closer to the central axis of the vessel.

The graphical data in FIGS. 6–9 shows the results of an actual flow study using the arrangement of transducers shown in FIG. 4. Time is shown on the horizontal axis of the graphs with a time scale of 0.5 seconds per division and the Doppler shift is shown on the vertical axis. From the waveforms shown in FIG. 6, it can be seen that the Doppler shifts in gates 1–5 measured by transducer T1 are similar while the Doppler shift measured in gate 6 is substantially lower due to the lower blood flow velocity close to the wall of the vessel. FIG.

7 shows the Doppler shifts obtained from transducer T2 which is disposed so that the beam therefrom extends at approximately 90° with respect to the longitudinal axis of the vessel. As can be seen, the Doppler shifts are indicated as being near zero as expected if the angle of the beam is a true 90°. The small Doppler shift readings obtained at the various sample volumes indicate that there was some angulation of the beam B2 with respect to the nominal 90° beam angle. However, at gate 2 where the beams B1 and B2 intersect, there is very little Doppler shift observed. As can be appreciated, the information from all 6 gates can be utilized for angle correction if desired. Alternatively, information from just a single gate, as for example, gate 2 can be utilized for angle correction.

FIG. 8 shows the diameter measurements for the lumen or flow passage of the vessel with the top curve representing the distance $D_B$ between the wall of the vessel and the back transducer T3. The second curve shows the distance $D_F+W$ which represents the thickness of the catheter C plus the distance from the transducer T2 to the wall of the vessel. The third curve shows the total diameter D which is equal to $D_B+D_F+W$. These curves show the variation in diameter between systole and diastole. In this case a mean value of 4.6 millimeters for $D_B$ and a mean value of 20.5 millimeters for $D_F+W$ gives a mean value of 25.1 millimeters for D.

FIG. 9 shows two traces with the upper trace or curve Q representing a continuous display of volumetric flow rate in liters per minute and showing the fluctuations in the flow rate between systole and diastole. A mean flow value of 4.5 liters per minute was obtained and this was found to correspond quite closely to the widely accepted Fick method of measurement. At the same time a series of thermodilution measurements showed flow values ranging from 4.5 to 5 liters per minute for the same patient.

The instantaneous angle error $\theta_{ERR}$ is shown in the lower trace of FIG. 9. The mean angle error was less than 1° with peak angle error of approximately 4°. In other patients, angle errors as high as 10° to 20° point to the necessity of angle correction or obtaining accurate flow measurement.

In connection with the present invention it has been found that in certain situations it is desirable to utilize a "pitch-catch" technique utilizing dual transducers. In the pitch-catch technique or mode, one transducer is utilized for transmitting ultrasonic pulses while the other is used for receiving the echoes. It has been found to be advantageous to incorporate an additional transducer and to utilize the pitch-catch technique in situations where the back side of the catheter is close to the vessel wall but not actually in contact with it. When there is a very short span between the catheter and the vessel wall, the residual ringing from the transmit burst can obscure the early received echoes. This problem can be avoided by providing physically separated transmitting and receiving transducers operating in the pitch-catch mode, thereby eliminating the need for the transmit burst and wall echo to be widely separated in time. Such an arrangement has been shown in FIG. 10 in which an additional transducer T4 has been provided adjacent the transducer T3 and generally on the opposite side of catheter C from the transducer T2. The pitch-catch mode is then used for back distance determination by way of measuring the time-of-flight for an ultrasonic pulse to propagate from transducer T3 to the vessel wall and back to transducer T4.

The pitch-catch technique can also be utilized for making velocity measurements as shown in FIG. 11 in which two transducers T1 and T2 have been provided in which the transducer T2 is disposed so that the relatively narrow beam B2 extending over approximately 10° propagates therefrom at approximately a 90° angle with respect to the wall of the vessel 151. This transducer T2 would be used for both transmitting and receiving. The A-mode signal received by transducer T2 would be utilized for making time-of-flight distance measurements to ascertain the diameter of the vessel in conjunction with the transducer T3 which also operates in both the transmit and receive modes. Furthermore, the Doppler shifted signal received by transducer T2 would be used as part of an angle correction scheme to compensate for any uncertainty in the transducer angles. The transducer T1, on the other hand, by virtue of its narrow dimension, acoustic lens, or curved surface is specifically designed to efficiently receive ultrasonic signals over a wide range of angles, as for example, angles ranging from approximately 5° to 60°. Thus, as the ultrasonic pulse transmitted by transducer T2 propagates across the vessel, ultrasonic signals are scattered by the moving red blood cells and the Doppler shifted echoes are received by transducer T1. In this way, each range gate Doppler velocity measurement is made at a different angle rather than at a fixed angle as with the previous embodiments hereinbefore described. In other words, the transmitting transducer T2 insonifies the blood at a fixed angle of approximately 90°, while the receiving transducer T1 receives the Doppler shifted echoes from the moving red blood cells over a range of different angles. For example, the first range gate which is in close proximity to the transducer T2 would be at a shallow receive angle as, for example, an angle of 5° with the angle progressively increasing at the other range gates until an angle of as much as 60° is reached. The pitch-catch velocity measurement method is subject to errors due to angle uncertainty in much the same manner as the previous method hereinbefore described. However, the same potential for correcting for angle errors is present in this embodiment of the invention with the only difference being that additional but similar calculations must be made.

A major advantage to the pitch-catch mode of velocity measurement though, is that it permits simultaneous measurement of velocity profile via the Doppler shifted signal received by transducer T1, vessel diameter via the A-mode signal received by transducer T2, and angle error via the Doppler shifted signal received by transducer T2. This eliminates the need for multiplexing between two separate transducers to make non-simultaneous vessel diameter and velocity profile measurements as in the previous embodiment hereinbefore described. A further advantage of the pitch-catch mode of operation is that the velocity profile is measured along a line defined by the beam B2 from transducer T2, the same line that defines the location of the vessel diameter measurement. Since the velocity profile measurement is made along the same path as the diameter measurement, there is no need to make an assumption of constant velocity profile along the length of a segment of vessel. Therefore cardiac output, for example, in short or curved main pulmonary arteries can be more accurately determined.

The Doppler equation for making velocity measurements in accordance with the embodiment of the invention shown in FIG. 11 is set forth below:

$$v_i = \frac{cf_i}{f_o(\cos\theta_2 + \cos\theta_{1i})} \quad \text{Equation 14}$$

where $f_i$ is the Doppler frequency measured for range gate i; $\theta_2$ is the transmit beam angle for transducer T2 (approximately 90°), and $\theta_{1i}$ is the receive angle for transducer T1 which varies from 5° to 60° depending on the range gate. The receive angle is defined by:

$$\theta_{1i} = \arctan\left(\frac{x_i}{h}\right) \quad \text{Equation 15}$$

where $x_i$ is the distance from range gate i to transmit transducer T2 and h is the fixed distance between transducers T1 and T2 along the catheter.

Another embodiment of the invention is shown in FIG. 12 in which an additional transducer T4 is provided on the side of the catheter C opposite the transducer T1. Like transducer T1, the transducer T4, by virtue of its narrow dimension, acoustic lens, or curved surface is designed to efficiently receive ultrasonic signals over a wide range of angles. This catheter configuration provides pitch-catch velocity measurements on both the front and back sides of the catheter C. Such an arrangement is advantageous because with the pitch-catch arrangement, diameter and velocity measurements can be simultaneously obtained without any requirement for multiplexing. Thus it is possible to obtain front and back diameter and velocity measurements using only two-way electronic multiplexing. If the pitch-catch mode is not utilized as in certain of the previous embodiments, four-way multiplexing would be necessary in order to obtain front and back velocity measurements along with front and back distance measurements.

The various transducer arrangements which have been hereinbefore described can be utilized in conjunction with the catheter 12 shown in FIG. 1. Thus in FIG. 1 there has been provided the two front transducers T1 and T2 and one back transducer T3. The arrangement shown in FIG. 1 for the catheter 12 is particularly adapted for use in connection with the human heart for making continuous cardiac output measurements in the pulmonary artery.

The catheter 12 can be inserted into the pulmonary artery into the position shown in FIG. 13 in a manner generally well known to those skilled in the art. For example, the catheter can be inserted in a jugular vein by advancing the guide wire to straighten the tip of the catheter. The catheter can then be introduced into the superior vena cava and into the heart 161 as shown in FIG. 13 by introducing it through the venous port 162 through the right atrium 164 through the tricuspid valve 166 through the right ventricle 167 and then through the pulmonary valve 168 through the main pulmonary artery 169 and then continuing into the right pulmonary artery branch 171 with the balloon 46 being disposed downstream. With the catheter 12 positioned in this manner, it can be seen that the front transducers T1 and T2 are disposed within the main pulmonary artery 169 or within the trunk below the bifurcation 172 and above the pulmonary valve 168.

The location of the tip of the catheter can be readily ascertained by those skilled in the art by monitoring the pressure waveforms from the distal pressure port 48 as the catheter is advanced through the heart. The position of the catheter can be confirmed by noticing the pressure waveform produced through port 54. This should be a pulmonary artery waveform when cardiac output flow measurements are to be obtained. With the catheter 12 in the position shown in FIG. 13, the velocity and diameter measurements can be readily accomplished in the manner hereinbefore described. With the confirmation of the pulmonary artery pressure waveform in port 54, the catheter will have a tendency to be closer to one wall than the other wall of the pulmonary artery. With the arrangement shown it is found that the bend 43 rests on the pulmonary artery bifurcation which facilitates the positioning of the transducers and port 54 in the main pulmonary artery.

The catheter 12 shown in FIG. 13, when the positioning device is removed, anatomical left wall comes closer to the the right wall as viewed in FIG. 13) of the main pulmonary artery 169 facing the right pulmonary artery branch 171. The catheter 12 is positioned in a manner such that the ultrasonic transducers T1, T2 and T3 are positioned such that the beams emanating therefrom lie substantially within a single plane which includes the longitudinal axis of the pulmonary artery so that accurate diameter and velocity measurements can be made in the manner hereinbefore described.

In the event it is desired that the catheter be disposed closer to the left side wall as viewed in FIG. 15,) it has been found that it is desirable to provide another embodiment of the catheter which is a catheter 176 which is shown in FIG. 14. This catheter 176 is provided with a flexible elongate element 177 similar to the elongate element 13 which has a relatively straight flexible portion 177a. The flexible elongate member 177 is provided with a distal extremity 178 which has a latex balloon 179 formed thereon. The distal extremity 178 has a curved portion 177b which forms an approximately 260° bend 181 which extends into another relatively straight portion 177c. It then extends through another curved portion 177d which forms an approximately 90° bend 182, a straight portion 177e and then a curved portion 177f which forms a relatively large radius bend 183 and then a relatively short straight portion 177g on which the balloon 179 is formed. The catheter 176 is also provided with a pulmonary artery pressure port 186 as well as the other ports (not shown) of the catheter 12 in FIG. 1.

When the catheter 176 of the configuration shown in FIG. 14 is introduced into the heart as shown in FIG. 15 the portion 177c is closer to the anatomical right wall (left wall as viewed in FIG. 15) of the main pulmonary artery 169 when the positioning device is in the retracted position allowing the catheter to hug that wall. With the arrangement shown it is found that the bend 181 rests on the tricuspid valve 166 which facilitates the catheter being moved closer to the anatomical right side of the pulmonary artery (left wall as viewed in FIG. 15) so that the catheter will not contact the moving ventricular wall 191 in FIG. 15.)

As illustrated in FIGS. 16–18, when the catheter 12 shown in FIG. 1 is inserted into the pulmonary artery 169, the shape and mechanical properties of this catheter cause it to position itself closer to the anatomical right side 181 of the arterial wall, as viewed in FIG. 16, with transducers T1 and T2 facing toward the anatomical right side of the arterial wall and transducer T3 facing toward the right side of the wall. Beams 182, 183 from transducers T2, T3 are thus generally perpendicular to the anatomical right and anatomical left sides of the arterial wall, and beam 184 from transducer T1 is directed down the artery toward the anatomical right wall. In this position, the catheter is typically spaced about 5–7 mm from the anatomical left side of the wall, and the information provided by beams 182 and 183 is utilized in determining the diameter of the artery. The information provided by beam 184 is utilized in determining the velocity within the artery. Beams 182–184 all lie substantially in a plane which includes the longitudinal axis of the main pulmonary artery.

FIGS. 19–21 further illustrate the position of the "huggy-type" catheter 176 of FIG. 14 within the pulmonary artery 169. As discussed above, the shape and mechanical properties of this catheter cause it to position itself closer to the anatomical right side 186 of the arterial wall, as viewed in FIG. 19, with transducers T1 and T2 facing toward the anatomical left side of the arterial wall and transducer T3 facing toward the anatomical right side of the wall. Beams 187, 188 from transducers T2, T3 are thus generally perpendicular to the anatomical left and anatomical right sides of the arterial wall, and beam 189 from transducer T1 is directed down the artery toward the anatomical left side of the wall. In this position, the information provided by beams 187 and 188 is utilized in determining the diameter of the artery, and the information provided by beam 189 is utilized in determining the velocity within the artery. Beams 187–189 all lie substantially in a plane which includes the longitudinal axis of the main pulmonary artery.

Although the flexible elongate member elements 13 and 177 which are used for the catheters 12 and 176 respectively have been described as being formed of plastic, it has been found that in accordance with the present invention that it may be desirable to utilize a certain type of plastic which has greater resilience and resistance to creep under stress. One such plastic found to be particularly suitable for catheters of the type herein described is PEBAX plastic, manufactured by Atochem, 4, cours Michelet La Défense, 10-Cedex 42, 92091 Paris, La Défense, France having a Shore D hardness ranging from 40D to 55D and preferably 48D. This material has been found to provide a number of advantages in connection with the present invention.

What is claimed is:

1. In a method for measuring volumetric flow rate of a liquid in a vessel having a wall and having an axis extending longitudinally of the vessel parallel to the vessel wall, by the use of having first and second ultrasonic transducers disposed on the front side of the catheter, positioning the catheter within the vessel and adjacent the wall of the vessel, making pulsed Doppler velocity profile measurements by beaming energy within the vessel from the first ultrasonic transducer to cross the longitudinal axis at an angle, making time of flight diameter measurement, simultaneously obtaining pulsed Doppler velocity measurements to derive angle error corrections by utilizing the second ultrasonic transducer to produce a beam of energy within the vessel which crosses the vessel generally perpendicular to the longitudinal axis of the vessel and combining the velocity profile and diameter measurements to determine the volumetric flow rate of liquid passing through the vessel.

2. A method as in claim 1 wherein a ratio of Doppler shift frequency components are measured from two or more angles along a given flow streamline to derive Doppler angle errors.

3. A method as in claim 2 wherein the true angle between the flow streamline and the ultrasound beam is derived and used in obtaining the velocity profile and diameter of the vessel.

4. A method as in claim 3 wherein the catheter is provided with a third transducer on the opposite back side of the catheter together with the step of making a time-of-flight distance measurement by emitting an ultrasonic beam from the third transducer which passes from the catheter to the back wall of the vessel, adding the first and second distance measurements with the diameter of the catheter to determine the diameter of the vessel for making the volumetric flow rate calculations.

5. A method as in claim 4 together with the step of providing the catheter with a fourth transducer on the back side of the catheter, utilizing one of the third and fourth transducers as a transmit transducer and the other of the third and fourth transducers as a receive transducer and utilizing the third and fourth transducers to make an A-mode time-of-flight back distance measurement.

6. A method as in claim 1 wherein the first transducer is provided with a narrow aperture, a lens or a curved surface and is only utilized as a receive transducer and wherein an ultrasonic beam emitted by the second transducer is received by the second transducer and is also received by the first transducer at different range gates extending across the diameter of the vessel so that there are provided a plurality of pulsed Doppler velocity measurements simultaneously with a time-of-flight diameter measurement.

7. A method as in claim 1 wherein the catheter is provided with back third and fourth transducers and in which the third transducer is utilized to make an A-mode time-of-flight back distance measurement and the fourth transducer is utilized to make back pulsed Doppler velocity measurements.

8. A method as in claim 1 wherein the catheter is positioned so that it is disposed generally towards the right side of the main pulmonary arterial wall.

9. A method as in claim 1 wherein the catheter is positioned so that it is disposed generally towards the left side of the main pulmonary arterial wall.

* * * * *

UNITED STATES PATENT AND TRADEMARK OFFICE
CERTIFICATE OF CORRECTION

PATENT NO. : 5,078,148

DATED : January 7, 1992

INVENTOR(S) : Nassi et al.

It is certified that error appears in the above-identified patent and that said Letters Patent is hereby corrected as shown below:

At col. 5, line 24, change "0.98" to --0.098--.
At col. 6, line 67, "cable 102" should be labeled in Figure 1.
At col. 8, line 21, delete --13c--.
At col. 9, line 14, change "witin" to --within--.
At col. 11, line 45, change "151" to --152--.
At col. 14, line 9, after "wall" insert --151--.
At col. 14, line 9, after "vessel", delete --151--.
At col. 15, line 10, change "$O_{1i}$" to --$\theta_{1i}$--.
At col. 16, lines 10-21, change "removed, anatomical left wall comes closer to the right wall" to --removed, comes closer to the anatomical left wall (the right wall--.
At col. 16, line 44, "straight portion 177e" should be labeled in Figure 14.
At col. 16, line 66, change "right side 181 of the arterial" to --left--.
At col. 16, line 66, change "viewed" to --shown--.
At col. 17, line 1, change "the right side" to --the left side--.

Signed and Sealed this

Twentieth Day of July, 1993

Attest:

MICHAEL K. KIRK

*Attesting Officer*     Acting Commissioner of Patents and Trademarks